US012806371B2

(12) United States Patent
Harding et al.

(10) Patent No.: US 12,806,371 B2
(45) Date of Patent: Nov. 24, 2026

(54) FLEXIBLE SHIELD FOR REDUCING TUBING BUCKLING IN BLOOD COLLECTION DEVICE

(71) Applicant: Becton, Dickinson and Company, Franklin Lakes, NJ (US)

(72) Inventors: Weston F. Harding, Lehi, UT (US); Shaun Lauer, Portland, OR (US); Serena Robinson Agrawal, Salt Lake City, UT (US); Evan Barbour VandenBrink, San Mateo, CA (US); Megan S. Scherich, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 999 days.

(21) Appl. No.: 17/972,774

(22) Filed: Oct. 25, 2022

(65) Prior Publication Data

US 2023/0134015 A1 May 4, 2023

Related U.S. Application Data

(60) Provisional application No. 63/273,252, filed on Oct. 29, 2021.

(51) Int. Cl.

*A61B 5/00* (2006.01)
*A61B 5/15* (2006.01)
(Continued)

(52) U.S. Cl.

CPC ... *A61M 25/0043* (2013.01); *A61B 5/150992* (2013.01); *A61M 25/0113* (2013.01); *A61M 2025/0059* (2013.01)

(58) Field of Classification Search

CPC .......... A61M 25/0043; A61M 25/0113; A61M 2025/0059; A61B 5/150992;
(Continued)

(56) References Cited

U.S. PATENT DOCUMENTS 5,501,675 A * 3/1996 Erskine ............ A61M 25/0631 604/164.12
5,897,533 A 4/1999 Glickman
(Continued)

FOREIGN PATENT DOCUMENTS

AU 2019351151 A1 * 4/2021 ............ A61B 5/153
CA 3158989 A1 * 6/2021 ........ A61M 25/0631
(Continued)

*Primary Examiner* — May A Abouelela
(74) *Attorney, Agent, or Firm* — The Webb Law Firm

(57) ABSTRACT

A medical device includes a catheter having proximal and distal ends, and defining a lumen, an introducer having proximal and distal ends, and defining an inner volume configured to movably receive the catheter. The distal end of the introducer has a lock configured to couple the introducer to an intravenous line, the introducer having a flexible member arranged within the inner volume configured to limit deflection of the catheter as the catheter is moved within the introducer, and an actuator movably coupled to the introducer. The actuator has a first portion disposed outside the introducer and a second portion disposed in the inner volume of the introducer and coupled to the catheter. The actuator configured to move relative to the introducer to move the catheter between first and second positions, such that the first portion is disposed within the intravenous line when the introducer is coupled to the intravenous line.

10 Claims, 9 Drawing Sheets

(51) Int. Cl.
*A61M 25/00* (2006.01)
*A61M 25/01* (2006.01)

(58) Field of Classification Search
CPC .......... A61B 5/15003; A61B 5/150259; A61B 5/150656; A61B 5/150809; A61B 5/150816; A61B 5/150824; A61B 5/153; A61B 5/150206
See application file for complete search history.

(56) References Cited

U.S. PATENT DOCUMENTS 6,712,790 B1 * 3/2004 Prestidge ........... A61B 5/15003 604/177
6,730,062 B2 * 5/2004 Hoffman ........... A61M 25/0631 604/164.02
9,415,186 B2 * 8/2016 Chebator .......... A61M 25/0668
10,744,303 B2 * 8/2020 Duindam .......... A61M 25/0133
11,090,461 B2 8/2021 Ehrenreich et al.
12,343,479 B2 * 7/2025 Yang ..................... A61M 5/007
12,377,248 B2 * 8/2025 Burkholz ........... A61M 25/0113
2006/0079809 A1 * 4/2006 Goldberger ...... A61B 5/150305 600/576
2007/0073160 A1 * 3/2007 Imam ................. A61B 5/15003 600/476
2007/0073271 A1 * 3/2007 Brucker .............. A61M 25/007 604/537
2008/0300576 A1 * 12/2008 Vitullo ............... A61M 25/0113 604/523
2009/0178459 A1 * 7/2009 Li .......................... C12Q 1/001 73/1.02
2009/0240197 A1 * 9/2009 Cowan ............... A61M 25/0116 604/528
2010/0210934 A1 * 8/2010 Belson ............... A61B 17/3421 604/164.11
2011/0313318 A1 * 12/2011 Rule ................ A61B 5/150389 600/581
2013/0114068 A1 * 5/2013 Lim ....................... A61B 5/153 356/246
2013/0165867 A1 * 6/2013 Isaacson .......... A61B 5/150992 604/534
2014/0257234 A1 * 9/2014 Ma .................... A61M 39/0606 604/500
2015/0165165 A1 * 6/2015 Rodriguez Lelis .......................... A61B 5/150992 600/576
2016/0220161 A1 * 8/2016 Goral .................... A61M 21/02
2016/0220791 A1 * 8/2016 Akcay .............. A61B 5/150259
2016/0271363 A1 * 9/2016 Bauer ............... A61M 25/0026
2017/0028171 A1 * 2/2017 Ishida ............... A61M 25/0668
2017/0028172 A1 * 2/2017 Ishida ............... A61M 25/0612
2017/0043132 A1 * 2/2017 Ishida ............... A61M 25/0606
2017/0056639 A1 * 3/2017 Ma ...................... A61M 25/002
2017/0216564 A1 * 8/2017 Devgon ............ A61M 25/0606
2017/0296112 A1 * 10/2017 Lim ....................... G01N 21/07
2018/0272107 A1 * 9/2018 Ehrenreich ...... A61B 5/150748
2018/0296149 A1 * 10/2018 Goral ............... A61B 5/150221
2019/0021640 A1 * 1/2019 Burkholz ............... A61B 5/153
2019/0321598 A1 * 10/2019 Harding .............. A61M 25/065
2019/0388616 A1 12/2019 Tominaga et al.
2020/0023176 A1 * 1/2020 Hu ......................... A61B 5/153
2020/0046948 A1 * 2/2020 Burkholz .......... A61M 25/0606
2020/0100716 A1 4/2020 Devgon et al.
2020/0170559 A1 * 6/2020 Burkholz ......... A61B 5/150992
2021/0000493 A1 1/2021 Badadamath et al.
2021/0052851 A1 2/2021 Devgon et al.
2021/0093837 A1 * 4/2021 Spearman .......... A61B 5/15003
2021/0228125 A1 * 7/2021 Ma .................... A61M 25/0028
2021/0228781 A1 * 7/2021 Scherich ................. A61L 31/16
2021/0290126 A1 * 9/2021 Burkholz ......... A61B 5/150992
2021/0290264 A1 * 9/2021 Harding ............. A61B 17/3423
2021/0298730 A1 * 9/2021 Baxter .............. A61M 25/0054
2021/0299408 A1 * 9/2021 Yong ................. A61M 25/0606
2021/0299426 A1 * 9/2021 Scherich .......... A61B 5/150992
2021/0393921 A1 * 12/2021 Burkholz .......... A61M 25/0017
2022/0032013 A1 * 2/2022 Howell ............. A61M 25/0606
2022/0110561 A1 * 4/2022 Blanchard .......... A61B 5/15003
2022/0168548 A1 * 6/2022 Dong .................... A61M 5/158
2022/0305236 A1 9/2022 Harding et al.
2022/0313958 A1 10/2022 Harding et al.
2022/0331562 A1 * 10/2022 Jaros ................. A61M 25/0097
2022/0354400 A1 * 11/2022 Teoh ................ A61B 5/150992

FOREIGN PATENT DOCUMENTS

CN 110446520 A * 11/2019 ........ A61M 25/0631
CN 113694352 A * 11/2021 .......... A61M 25/003
CN 216395002 U * 4/2022 .......... A61M 25/065
KR 20220062280 A * 5/2022 ....... A61B 5/150992

* cited by examiner

FLEXIBLE SHIELD FOR REDUCING TUBING BUCKLING IN BLOOD COLLECTION DEVICE

CROSS-REFERENCE TO RELATED APPLICATION

The present application claims priority to U.S. Provisional Application Ser. No. 63/273,252, entitled "Flexible Shield for Reducing Tubing Buckling in Blood Collection Device", filed Oct. 29, 2021, the entire disclosure of which is hereby incorporated by reference in its' entirety.

BACKGROUND OF THE INVENTION

Field of the Invention

The present disclosure relates generally to medical devices for use with intravenous (IV) catheters and, more specifically, to medical devices with features for limiting deflection of flexible catheters.

Description of Related Art

Blood collection devices, when used with indwelling IV catheters, can include displaceable catheters that are advanced beyond the tip of the indwelling catheter for blood collection. Often, when the displaceable catheter is advanced, it can encounter an obstruction, resulting in deflection of the catheter. Examples of obstructions include the friction of the seal within the blood collection device, torturous path within an integrated catheter, pinching of the catheter tubing as it dives into the skin, thrombus, fibrin, and valves. Such deflections can reduce the ability of the displaceable catheter to extend beyond the tip of the indwelling catheter, and thus limits their use for blood collection. Accordingly, a need exists in the art for devices that limit buckling, and that ensure timely and effective blood collection.

SUMMARY OF THE INVENTION

Provided herein is a medical device, including a catheter having a proximal end, a distal end, and a sidewall therebetween defining a lumen therethrough, an introducer having a proximal end, a distal end, and a sidewall therebetween defining an inner volume configured to movably receive the catheter, the distal end of the introducer having a lock configured to couple the introducer to an intravenous line, the introducer further having a flexible member arranged within the inner volume configured to limit deflection of the catheter as the catheter is moved within the introducer, and an actuator movably coupled to the introducer, the actuator having a first portion disposed outside of the introducer and a second portion disposed in the inner volume of the introducer and coupled to the catheter, the actuator configured to move relative to the introducer to move the catheter between a first position, in which the catheter is disposed within the introducer, and a second position, in which the distal end of the catheter is disposed beyond the distal end of the introducer such that at least a first portion of the catheter is disposed within the intravenous line when the introducer is coupled to the intravenous line.

In certain configurations, the flexible member is arranged along a longitudinal axis within the inner volume of the introducer. The flexible member may include an elastomeric material. In certain configurations, the flexible member and the introducer define a substantially cylindrical passage within which the catheter is received. The flexible member may extend from the proximal end of the introducer to the distal end.

In certain configurations, the flexible member is a unitary member. In other configurations, the flexible member may include a plurality of flexible members. The plurality of flexible members may be arranged about a perimeter of the inner volume. The plurality of flexible members may substantially surround the catheter.

In other configurations, as the actuator is moved toward the distal end of the introducer, the second portion of the actuator displaces the flexible member. The second portion of the actuator may be coupled to the proximal end of the catheter. In still other configurations, a lubricant may be received within the inner volume.

Also provided herein is a medical device, including a catheter having a proximal end, a distal end, and a sidewall therebetween defining a lumen therethrough, an introducer having a proximal end, a distal end, and a sidewall therebetween defining an inner volume configured to movably receive the catheter, the distal end of the introducer having a lock configured to couple the introducer to an intravenous line, the introducer further having a flexible member arranged within the inner volume, and an actuator coupled to the catheter, the actuator configured to move relative to the introducer in response to a first force exerted on the actuator to move the catheter between a first position, in which the distal end of the catheter is disposed within the lumen of the lock, and a second position, in which the catheter extends through the lock and intravenous line when the lock is coupled to the intravenous line such that the distal end of the catheter is disposed within the intravenous line, wherein the actuator is configured to exert a second force different from the first force on the proximal end of the catheter as the actuator moves the catheter from the first position to the second position, the second force resulting in a deflection of a portion of the catheter disposed between the actuator and the lock as the actuator moves the catheter from the first position to the second position, and wherein the flexible member is configured to limit the deflection.

In certain configurations, the actuator includes a first portion disposed outside of the introducer and a second portion disposed within the introducer, and the first force exerted on the actuator is exerted on the first portion of the actuator, the second force exerted by the actuator is exerted by the second portion of the actuator. The flexible member may be arranged along a longitudinal axis within the inner volume of the introducer. Optionally, the flexible member may include an elastomeric material.

In certain configurations, the flexible member and the introducer may define a substantially cylindrical passage within which the catheter is received. The flexible member may extend from the proximal end of the introducer to the distal end. The flexible member may be a unitary member. In certain configurations, the flexible member may include a plurality of flexible members. Optionally, the plurality of flexible members may be arranged about a perimeter of the inner volume. In other configurations, the plurality of flexible members may substantially surround the catheter.

In certain configurations, as the actuator is moved toward the distal end of the introducer, the second portion of the actuator displaces the flexible member. The second portion of the actuator may be coupled to the proximal end of the catheter. The device may further include a lubricant received within the inner volume.

Also provided herein is a medical device, including a catheter having a proximal end, a distal end, and a sidewall therebetween defining a lumen therethrough, an introducer having a proximal end, a distal end, and a sidewall therebetween defining an inner volume configured to movably receive the catheter, the distal end of the introducer having a lock configured to couple the introducer to an intravenous line, the inner volume configured to limit deflection of the catheter as the catheter is moved within the introducer, an actuator movably coupled to the introducer, the actuator having a first portion disposed outside of the introducer and a second portion disposed in the inner volume of the introducer and coupled to the catheter, the actuator configured to move relative to the introducer to move the catheter between a first position, in which the catheter is disposed within the introducer, and a second position, in which the distal end of the catheter is disposed beyond the distal end of the introducer such that at least a first portion of the catheter is disposed within the intravenous line when the introducer is coupled to the intravenous line.

DESCRIPTION OF THE INVENTION

Figure 1:
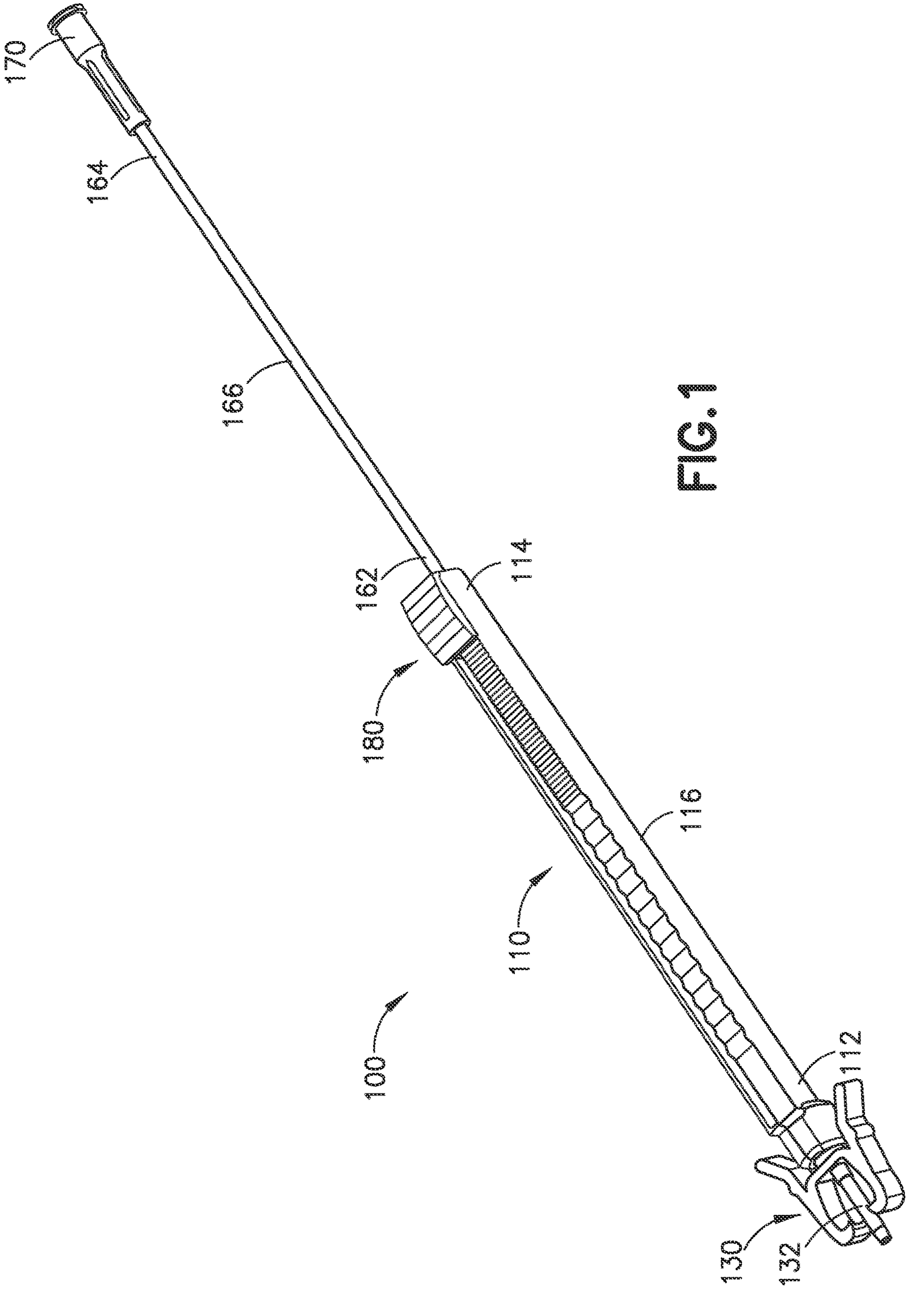
FIG. 1 is a perspective view of a medical device according to non-limiting embodiments described herein.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

It should be understood that any numerical range recited herein is intended to include all values and sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

U.S. Pat. No. 11,090,461, which discloses medical devices including fluid transfer devices, is incorporated by reference herein in its entirety.

Provided herein is a medical device with a displaceable medical implement, such as a displaceable catheter. Exemplary medical devices include those utilized for blood collection from indwelling IV catheters, such as peripheral IV catheters, and have displaceable catheters that can be displaced such that a tip of the displaceable catheter extends beyond a tip of the indwelling IV catheter. In some instances, the displaceable catheter can encounter a resistive force, whether in the form of an occlusion at the tip of the indwelling IV catheter, a thrombus within the blood vessel, friction within the medical device, pinching of the catheter as the catheter curves to match the angle at which the IV catheter enters the patient's skin, or combinations thereof. Such resistive forces can result in deflection (e.g., buckling) of the displaceable catheter. Accordingly, devices as described herein include features for limiting deflection of displaceable implements (e.g., catheters) in medical devices.

Turning to FIGS. 1-4, shown is a non-limiting embodiment of a medical device 100. While exemplified as a fluid transfer device, those of skill in the art will appreciate that the deflection-limiting features described herein will be suitable for any medical device with a displaceable implement that is subject to deflection, for example flexible, displaceable components. In the illustrated non-limiting embodiment, medical device 100 includes an introducer 110 having a distal end 112 and a proximal end 114, with a sidewall 116 therebetween defining an inner volume 118. As shown in FIGS. 6-12, inner volume 118 may include a first portion 118*a* and a second portion 118*b*, which may or may not be fluidly isolated from one another. Introducer 110 may include, at distal end 112 thereof, a lock 130 and blunt cannula 132, for coupling to an IV catheter (not shown), a catheter adapter (not shown), or the like. Introducer 110 may be any suitable size and/or shape, and may be formed of any suitable material(s), such as plastic(s). While lock 130 is exemplified in the present figures as a plurality of arms and blunt cannula 132, those of skill will appreciate that any connection or coupling, for example a luer, can be used, so long as distal end 152 of catheter 150 may pass through the connection to access a medical device, such as an IV catheter to which introducer 110 is coupled.

Figure 2:
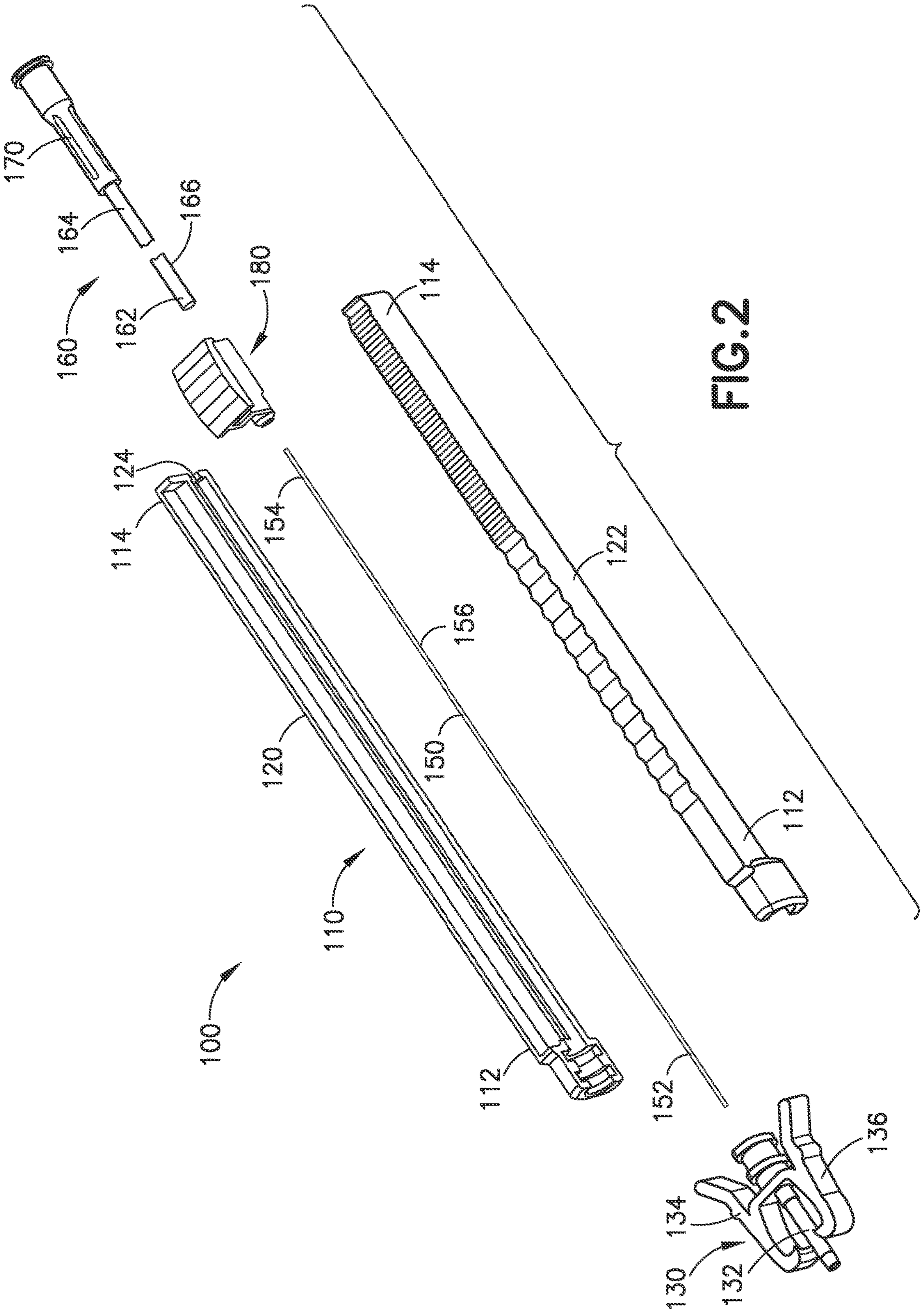
FIG. 2 is an exploded perspective view of a medical device according to non-limiting embodiments described herein.
Figure 3:
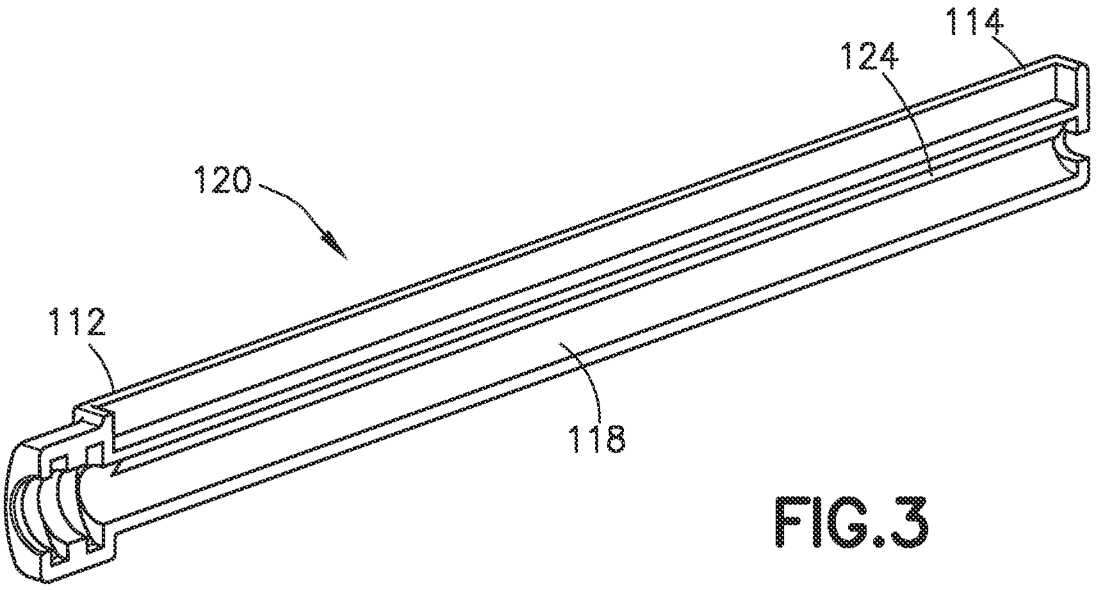
FIG. 3 is an exploded perspective view of a medical device according to non-limiting embodiments described herein.
Figure 4:
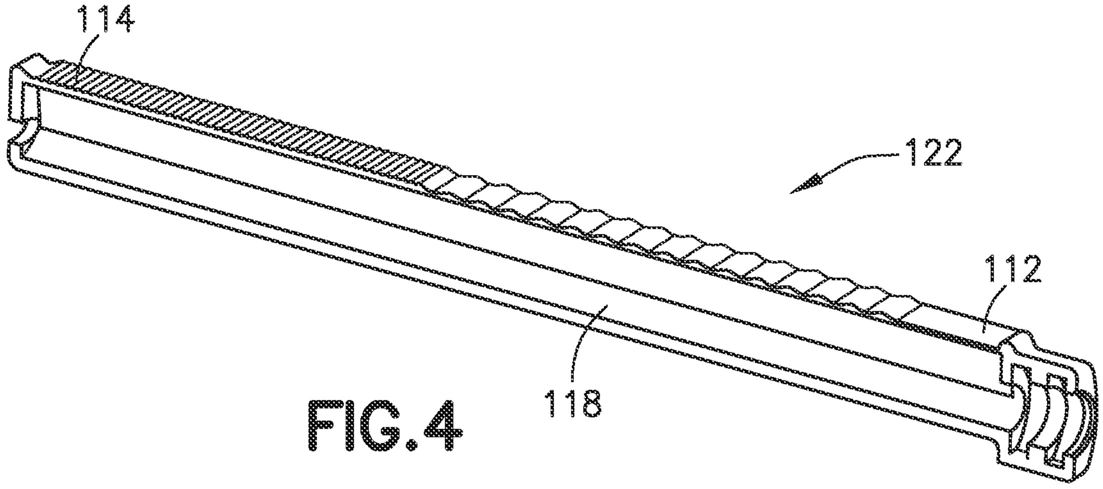
FIG. 4 is an exploded perspective view of a medical device according to non-limiting embodiments described herein.

With reference to FIGS. 2-4, introducer 110 may be formed of two housing portions, a first housing portion 120 and a second housing 122. First and second housing portions 120, 122 can be coupled together by any suitable method, for example a snap fit, friction fit, ultrasonic weld, and/or adhesive. Combined housing portions 120, 122 may define inner volume 118, and one or more features on interior surfaces of housing portions 120, 122 may define first and second inner volume portions 118*a*, 118*b*.

Medical device 100 may further include one or more catheters. In the non-limiting embodiments illustrated in the attached drawings, medical device 100 includes a catheter 150 and, optionally, a secondary catheter 160. Secondary catheter 160 may be used to couple with, for example through coupler 170, a vacuum (air or liquid) source, a blood collection tube, a fluid reservoir, fluid source, syringe, and/or the like, which in turn, may place the catheter 150 in fluid communication therewith. Those of skill in the art will appreciate that multiple catheters need not be employed (e.g., a coupler, such as coupler 170, may be provided on proximal end 114 of introducer 110).

Catheter 150 may have a distal end 152, proximal end 154, and a sidewall 156 therebetween defining a lumen therethrough. Catheter 150 may be of any suitable length and gauge, and may be formed of any suitable material in any suitable configuration (e.g., braiding). In non-limiting embodiments, catheter 150 is from 10-30 gauge, all values and subranges therebetween inclusive. In non-limiting embodiments, catheter 150 may be formed of a relatively flexible biocompatible material with a Shore durometer of about 20 Shore A to 50 Shore D; about 20 Shore A to 95 Shore D; about 70 Shore D to 85 Shore D, and/or any other suitable range of Shore durometer. In some embodiments, at least a portion of catheter 150 may be formed of a braided material or the like, which can modify, change, and/or alter a flexibility of catheter 150 in response to a bending force or the like. In non-limiting embodiments, catheter 150 is formed of a polyimide-containing material. In non-limiting embodiments, catheter 150 is of a pre-determined length such that, when fully displaced distally, distal end 152 extends beyond a distal end of an IV catheter. In non-limiting embodiments, the predetermined length may be indicated by one or more indicia on introducer 110.

Secondary catheter 160 may have a distal end 162, proximal end 164, and a sidewall 166 defining a secondary lumen therethrough. As noted above, secondary catheter 160 may include a coupler 170 at proximal end 164 thereof. Coupler 170 may be any suitable connection or coupler, for example a luer, a needleless connector, or like connector known to those of skill in the art. Secondary catheter 160 may be of any suitable length and gauge, and may be formed of any suitable material in any suitable configuration (e.g., braiding). In non-limiting embodiments, secondary catheter 160 is from 10-30 gauge, all values and subranges therebetween inclusive. In non-limiting embodiments, secondary catheter 160 is a polyimide-containing material. In non-limiting embodiments, secondary catheter 160 is in fluid communication with catheter 150. In non-limiting embodiments, catheter 150 and secondary catheter 160 are configured to place a fluid reservoir, such as a blood collection tube (e.g., an evacuated tube) in fluid communication with the IV catheter, thus allowing for blood to be collected from the IV catheter.

Figure 8:
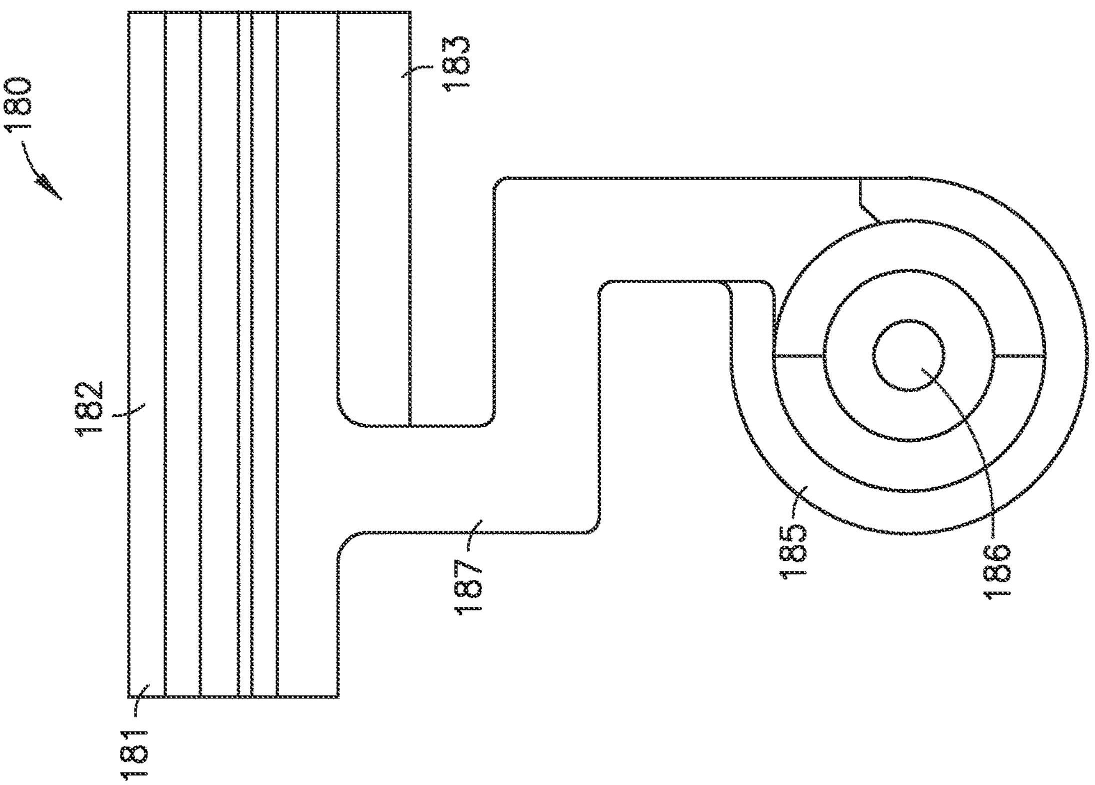
FIG. 8 is a front view of an actuator for a medical device according to non-limiting embodiments described herein.

Medical device 100 may also include an actuator 180, which may be coupled to catheter 150. In non-limiting embodiments, actuator 180 is coupled to proximal end 154 of catheter 150. Actuator 180 may be manipulated by a user, such as a medical professional, to transition the device 100 from a first configuration, in which distal end 152 of catheter 150 is proximal of the IV catheter, to a second configuration in which at least distal end 152 of catheter 150 is disposed in a distal position relative to the IV catheter. With reference to FIG. 8, shown is a non-limiting embodiment of actuator 180, in which actuator 180 includes a first portion 181 having an engagement member 182 and tab 183, second portion 185 including opening 186, and wall 187 therebetween. Engagement member 182 may be configured to be contacted by a finger of a user. Wall 187 may connect first portion 181 and second portion 185. As can be appreciated from the attached drawings, inner volume 118 of introducer 110 can have a tortuous cross-sectional shape. Wall 187 may be configured to match such a tortuous shape. Opening 186 may be included in second portion 185, and may be coupled with catheter 150 at any position along a length thereof. Coupling between catheter 150 and opening 186 may be accomplished through any known means, for example friction fit, ultrasonic weld, adhesives, or combinations thereof. Tab 183 may include one or more features that interact with an outer surface of introducer 100, for example, to provide tactile, acoustic, and/or visual feedback. Such feedback can inform a user, for example, of how far catheter 150 has been displaced, including whether distal end 152 of catheter 150 is in a distal position relative to the IV catheter.

In non-limiting embodiments, in use, a first force is exerted on actuator 180 by a user to move actuator 180 relative to introducer 110 to advance catheter 150 from a first position, in which distal end 152 of catheter 150 is disposed within a lumen defined by lock 130, toward a second position. A second force, different from the first force, is exerted by actuator 180, for example by virtue of interaction between second actuator portion 185 and catheter 150, on catheter 150, for example on proximal end 154 of catheter 150, as actuator 180 is advanced, displacing catheter 150 from the first position toward the second position.

Figure 5:
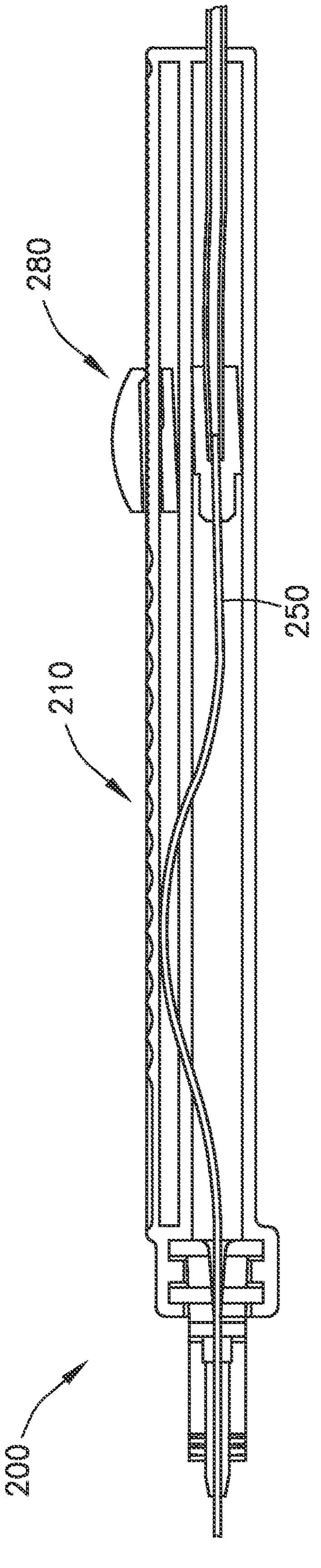
FIG.5 PRIOR ART
FIG. 5 is a cross-sectional view of a prior medical device.
Figure 6:
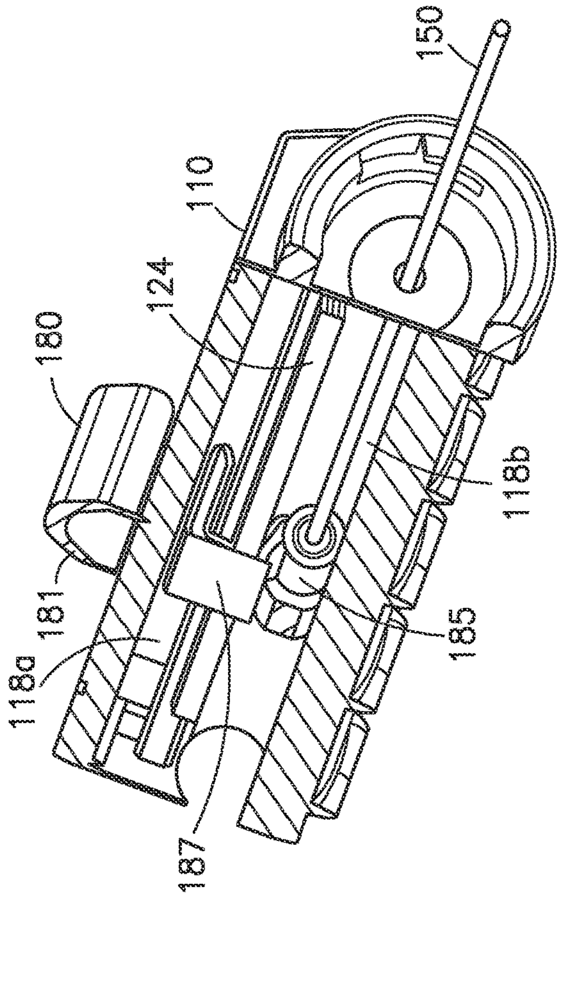
FIG. 6 is a cross-sectional view of a medical device according to non-limiting embodiments described herein.

As shown in FIG. 5, in prior devices 200, catheter 250 may be deflected if catheter 250 encounters an obstruction during deployment by actuator 280 and/or if there is friction between catheter 250 and any portion of device 200, as described previously. This deflection can increase beyond an acceptable amount, resulting in an inability to move distal end of catheter 250 to the second position (a distal position relative to the IV catheter). As shown in FIGS. 2-4, 6, 7, and 9, introducer 110 of medical device 100 may include a flexible member 124 arranged within inner volume 118 to limit deflection of catheter 150. Without wishing to be bound by the theory, it is believed that reducing the volume in which catheter 150 resides allows for an increase in force that can be applied to catheter 150, to bypass occlusions or blockages without an unacceptable level of deflection being exhibited.

Flexible member 124 may be connected to introducer 110 through a snap fit, friction fit, ultrasonic weld, adhesives, or combinations thereof. Flexible member 124 may be arranged within introducer 110 in any suitable configuration, so long it serves to limit deflection of catheter 150. In non-limiting embodiments, flexible member 124 extends along a substantial (e.g., more than 50%) length of introducer 110. In some embodiments, flexible member 124 extends along the complete length of the inner volume 118 of introducer 110. In some embodiments, flexible member 124 may mark a separation between inner volume first portion 118*a* and inner volume second portion 118*b*. Flexible member 124 may be formed of any suitable material. In non-limiting embodiments, flexible member 124 is formed of a material that allows flexible member 124 to maintain sufficient flexibility to allow flexible member 124 to be displaced by actuator 180 (e.g., wall 187) as actuator moves catheter 150 through inner volume 118. In non-limiting embodiments, flexible member 124 is formed of a material with sufficient resiliency such that flexible member 124 returns to its original configuration following transit of actuator 180, thereby maintaining a barrier that limits deflection of catheter 150 within inner volume 118.

Figure 7:
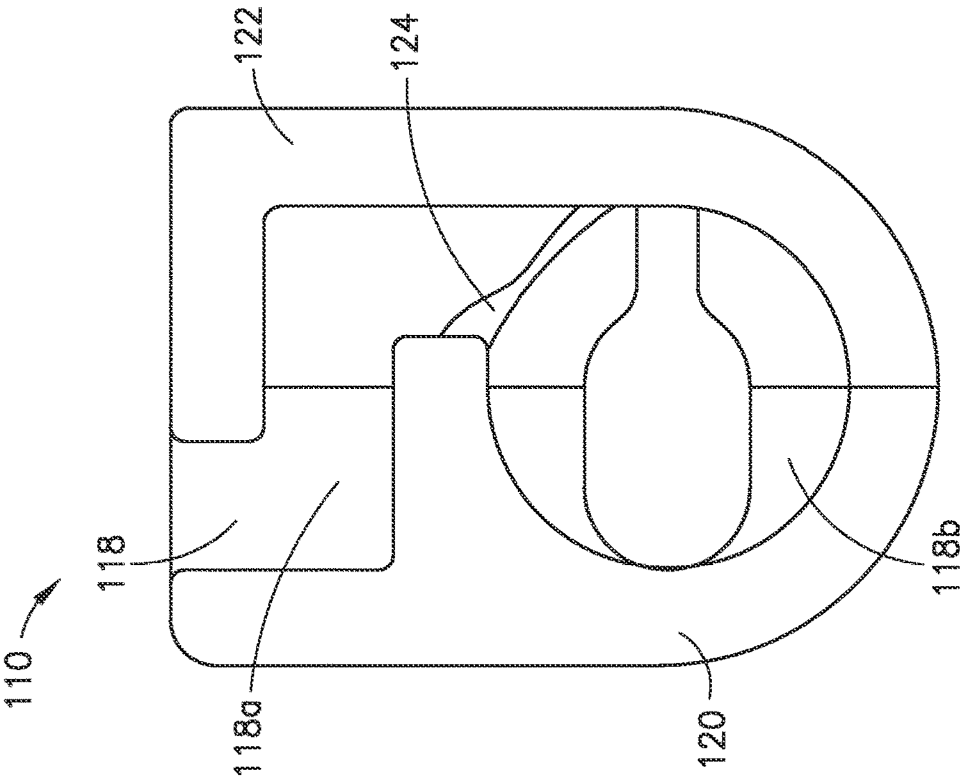
FIG. 7 is a cross-sectional view of a medical device according to non-limiting embodiments described herein.
Figure 9:
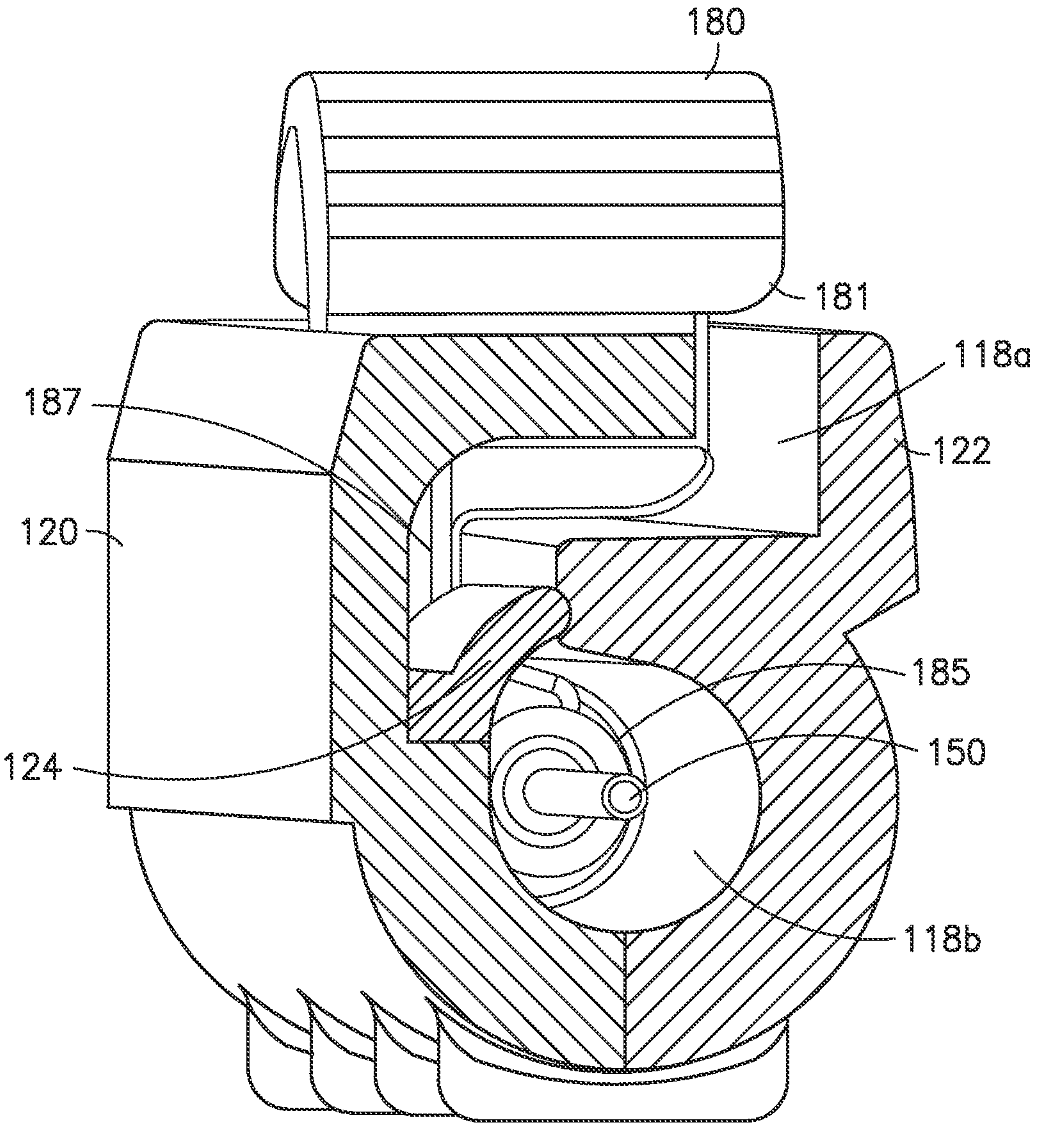
FIG. 9 is a cross-sectional view of a medical device according to non-limiting embodiments described herein.

With regard to FIG. 2, while flexible member 124 is shown as being connected to and/or part of first introducer housing portion 120, those of skill in the art will appreciate that flexible member 124 may be connected to one or both housing portions 120, 122, and may assume any orientation/angle relative thereto, so long as flexible member 124 limits deflection of catheter 150. For example, as shown in FIGS. 7 and 9, flexible member 124 may be oriented in a number of distinct ways in terms of angle and connection to one or more housing portions, and may, in some embodiments, form a border within inner volume 118, providing an inner volume second portion 118*b* that provides catheter 150 with less space than a total space of inner volume 118 within which deflection can occur.

Figure 10:
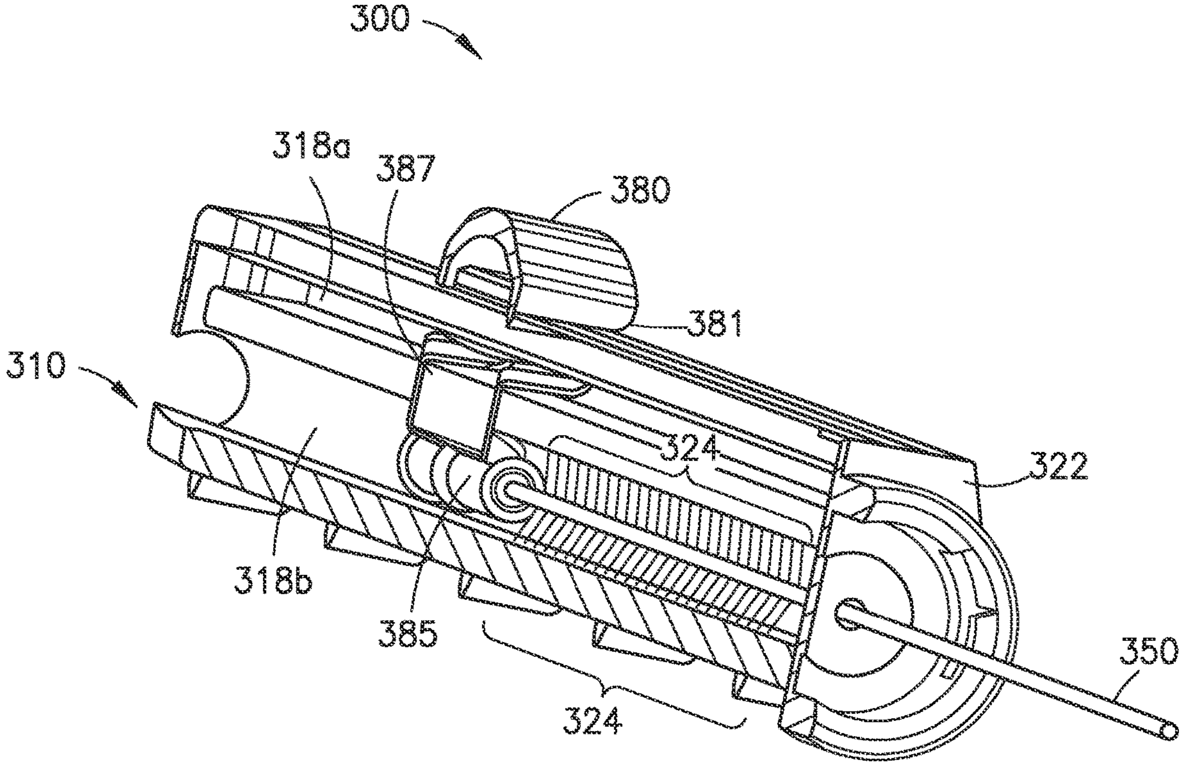
FIG. 10 is a cross-sectional view of a medical device according to non-limiting embodiments described herein.
Figure 11:
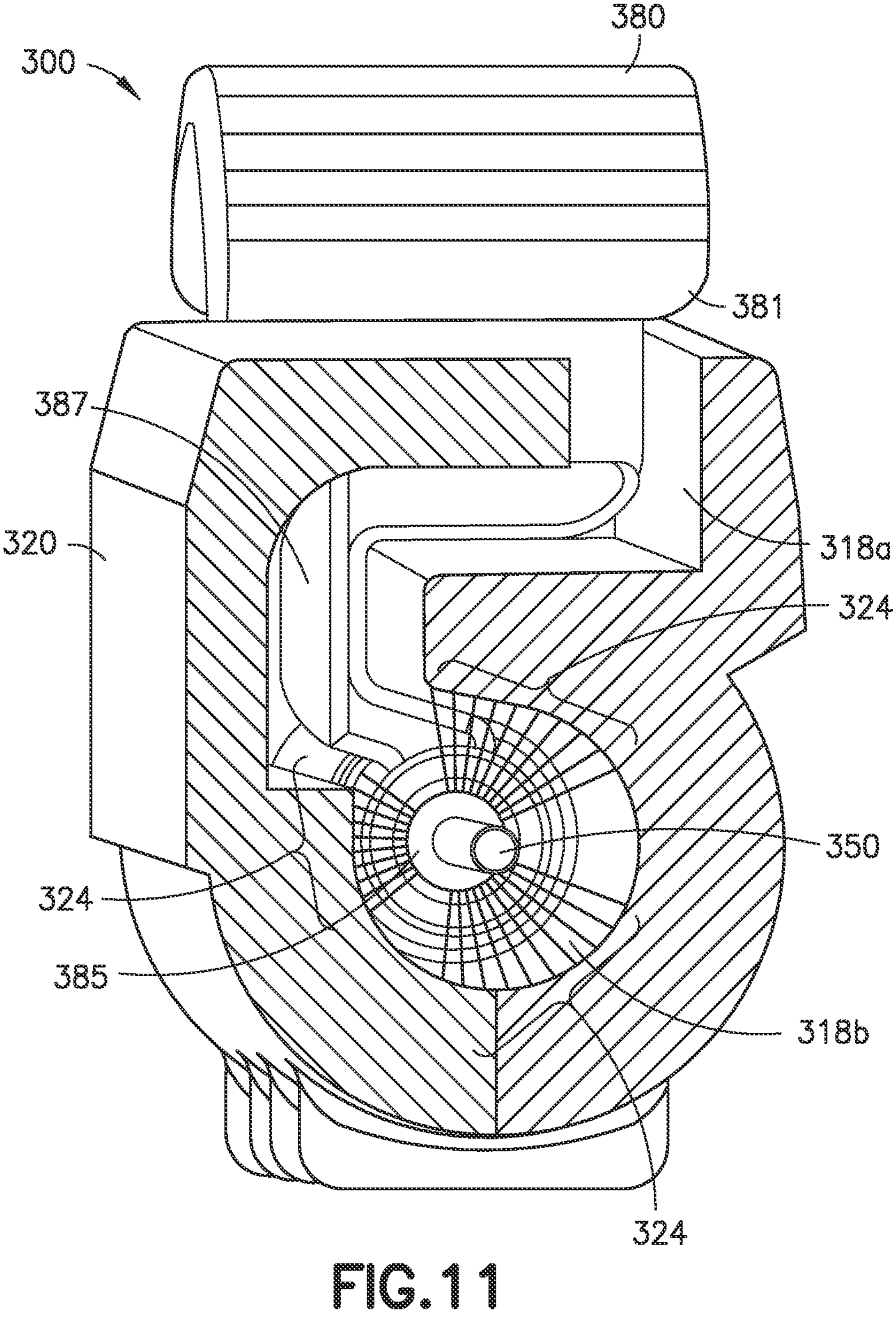
FIG. 11 is a cross-sectional view of a medical device according to non-limiting embodiments described herein.

Turning to FIGS. 10 and 11, shown is a non-limiting embodiment of a medical device 300. As described above, medical device 300 may include introducer 310, catheter 350, and actuator 380. Introducer may include a plurality of housing portions, such as first housing portion (not shown) and a second housing portion 322 defining an inner volume, optionally an inner volume including first inner volume portion 318*a* and second inner volume portion 318*b*. Actuator 380 may include a first portion 381, second portion 385, and wall 387 connecting first portion 381 and second portion 385. While not shown, medical device 300 may also include one or more features described in other embodiments, for example a secondary catheter and a lock (optionally with a blunt cannula) at distal end thereof.

In the non-limiting embodiments of FIGS. 10 and 11, medical device 300 further may include a plurality of flexible members, in the form of flexible fibers 324. Flexible fibers 324 may be connected with introducer 310 through friction fit, ultrasonic weld, adhesives, or combinations thereof. Flexible fibers 324 may be formed of any suitable material capable of limiting deflection of catheter 350. In non-limiting embodiments, flexible fibers 324 are formed of a silicone-containing material. In non-limiting embodiments, flexible fibers 324 are arranged within inner volume of introducer 310, for example in second inner volume 318*b*, in any suitable angular orientation. In non-limiting embodiments, flexible fibers 324 are arranged substantially about a perimeter (e.g., circumference) of second inner volume portion 318*b*. In non-limiting embodiments, flexible fibers 324 are arranged within second inner volume portion 318*b* in a manner that substantially or completely surrounds catheter 350. As with other embodiments of flexible member disclosed herein, plurality of flexible fibers 324 may be formed of a material that allows flexible fibers 324 to maintain sufficient flexibility to allow flexible fibers 324 to be displaced by actuator 380 (e.g., wall 387) as actuator moves catheter 350 through inner volume of introducer 310. In non-limiting embodiments, flexible fibers 324 may be formed of a material with sufficient resiliency such that flexible fibers 324 return to their original orientation following transit of actuator 380, thereby limiting deflection of catheter 350 within inner volume of introducer 310.

Figure 12A:
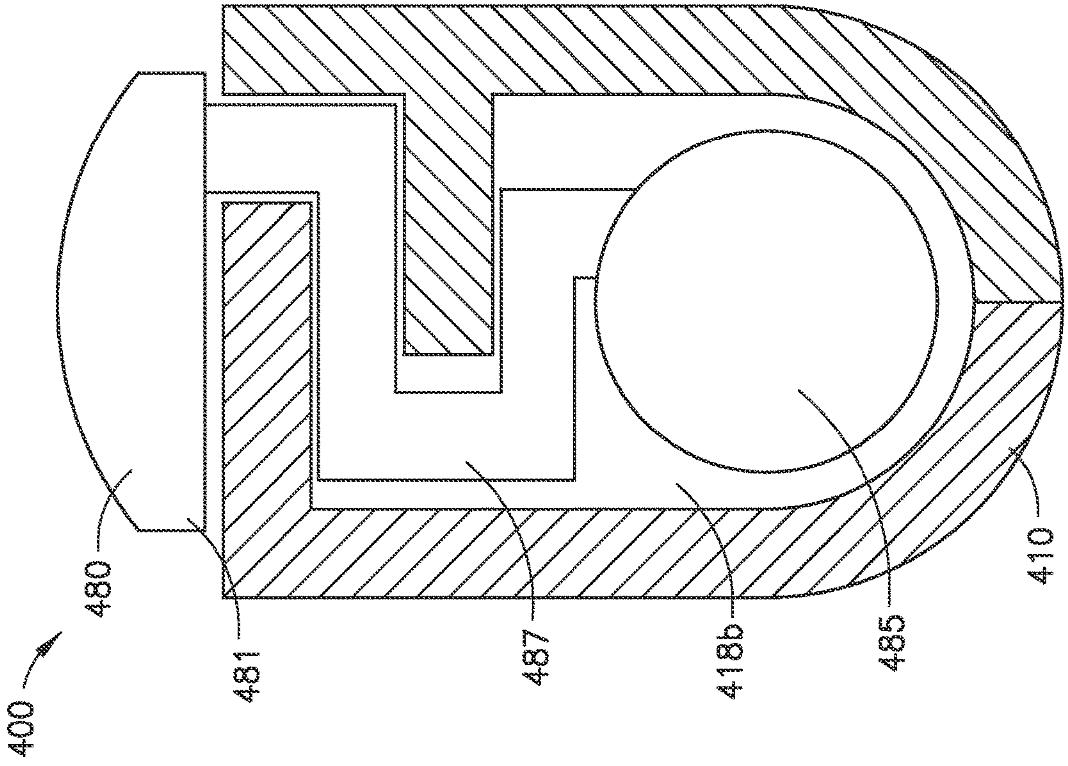
FIG. 12A PRIOR ART
FIG. 12A is a cross-sectional view of a prior medical device.
Figure 12B:
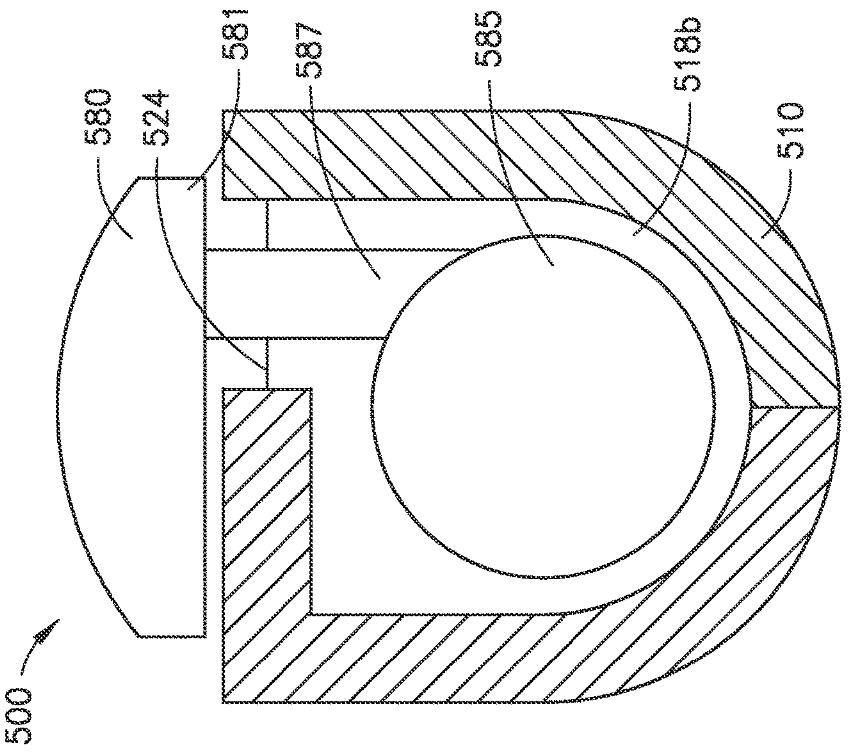
FIG. 12B is a cross-sectional view of a medical device according to non-limiting embodiments described herein.

Turning to FIG. 12A, shown is a cross-section view of an existing medical device 400. As can be appreciated, the inner volume of the medical device 400 is tortuous, and the configuration of actuator 480 matches this tortuous geometry, for example arrangement of wall 487. This arrangement can require a larger volume 418*b* surrounding a catheter (not shown), which can allow for greater deflection of a catheter or other medical implement during displacement thereof. Shown in FIG. 12B is a medical device 500 with a simplified inner geometry of introducer 510. As can be appreciated by the non-limiting embodiment of FIG. 12B, the simplified inner geometry allows for a reduced volume 518*b* as compared to known devices (418*b*, as shown in FIG. 12A). As also shown in FIG. 12B, the simplified geometry allows for a simplified actuator 580, for example a linear, non-tortuous wall 587 connecting actuator first portion 581 with actuator second portion 585. While one non-limiting configuration of inner volume 518*b* is shown in FIG. 12B, those of skill will appreciate that various cross-sectional shapes can be accommodated, so long as the volume in which a catheter or other medical implement can be deflected is minimized. In non-limiting embodiments, a barrier 524, for example such as a flexible member described herein, can be included, further limiting the ability of a medical implement, such as a displaceable catheter.

In non-limiting embodiments, introducer 510 with a simplified geometry includes a plurality of housing portions, for example as described herein. In non-limiting embodiments, the simplified geometry may require the introducer housing portions to be connected with an ultrasonic weld or adhesive, rather than through a snap or friction fit as is possible with known devices, such as those shown in FIG. 12A.

With regard to each non-limiting embodiment described herein, one or more additional elements for reducing deflection of a medical implement, such as a displaceable catheter, may be employed. For example, one or more lubricants can be included within introducer interior, on an exterior surface of the medical implement, and/or both. Those of skill in the art will appreciate that any suitable lubricant can be used. In non-limiting embodiments, the lubricant is a silicone-containing lubricant. In non-limiting embodiments or aspects, the lubricant is a polydimethylsiloxane-containing lubricant. In addition, one or more additional supporting structures, for example ribs, protrusions, or the like, may be included within introducer interior. Such structures may be arranged at one or more locations along a longitudinal axis of introducer, limiting the volume within which the medical implement, such as a catheter, can be deflected. In non-limiting embodiments, introducer may be molded with one or more supporting structures. In non-limiting embodiments, one or more supporting structures can be overmolded or attached to introducer through an adhesive, ultrasonic weld, or the like.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. A medical device, comprising:

a catheter having a proximal end, a distal end, and a sidewall therebetween defining a lumen therethrough;

an introducer having a proximal end, a distal end, and a sidewall therebetween defining an inner volume configured to movably receive the catheter, the distal end of the introducer having a lock configured to couple the introducer to an intravenous line, the introducer further having a flexible member arranged within the inner volume configured to limit deflection of the catheter as the catheter is moved within the introducer, the flexible member coupled to the proximal end of the introducer and the distal end of the introducer;

an actuator movably coupled to the introducer, the actuator having a first portion disposed outside of the introducer and a second portion disposed in the inner volume of the introducer and coupled to the catheter, the actuator configured to move relative to the introducer to move the catheter between a first position, in which the catheter is disposed within the introducer, and a second position, in which the distal end of the catheter is disposed beyond the distal end of the introducer such that at least a first portion of the catheter is disposed within the intravenous line when the introducer is coupled to the intravenous line; and wherein, as the actuator is moved toward the distal end of the introducer, the second portion of the actuator displaces the flexible member.

2. The device of claim 1, wherein the flexible member is arranged along a longitudinal axis within the inner volume of the introducer.

3. The device of claim 1, wherein the flexible member comprises an elastomeric material.

4. The device of claim 1, wherein the flexible member and the introducer define a substantially cylindrical passage within which the catheter is received.

5. The device of claim 1, wherein the flexible member is a unitary member.

6. The device of claim 1, wherein the flexible member comprises a plurality of flexible members.

7. The device of claim 6, wherein the plurality of flexible members are arranged about a perimeter of the inner volume.

8. The device of claim 6, wherein the plurality of flexible members substantially surrounds the catheter.

9. The device of claim 1, wherein the second portion of the actuator is coupled to the proximal end of the catheter.

10. The device of claim 1, further comprising a lubricant received within the inner volume.

* * * * *